(12) United States Patent
Mallela et al.

(10) Patent No.: US 8,318,933 B2
(45) Date of Patent: Nov. 27, 2012

(54) PROCESS FOR PREPARING ROSUVASTATIN CALCIUM

(75) Inventors: Sambhu Prasad Sarma Mallela, Hyderabad (IN); Narayan K. A. S. S. Garimella, Hyderabad (IN); Sukumar Nandi, Hyderabad (IN); Sunil Kumar Buridipad, Hyderabad (IN); Gangadhar Bhima Shankar Nangi, Hyderabad (IN); Ramesh Dandala, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 282 days.

(21) Appl. No.: 12/312,100

(22) PCT Filed: Oct. 29, 2007

(86) PCT No.: PCT/IB2007/003312
§ 371 (c)(1),
(2), (4) Date: Apr. 25, 2009

(87) PCT Pub. No.: WO2008/053334
PCT Pub. Date: May 8, 2008

(65) Prior Publication Data
US 2010/0048899 A1 Feb. 25, 2010

(30) Foreign Application Priority Data
Oct. 31, 2006 (IN) .......................... 1994/CHE/2006

(51) Int. Cl.
*C07D 239/02* (2006.01)
(52) U.S. Cl. ...................................... 544/297
(58) Field of Classification Search .................. 544/332, 544/297
See application file for complete search history.

(56) References Cited

U.S. PATENT DOCUMENTS

| | | | |
|---|---|---|---|
| 5,260,440 A | 11/1993 | Hirai | |
| RE37,314 E | 8/2001 | Hirai et al. | |
| 7,208,623 B2 | 4/2007 | Sedelmeier et al. | |
| 7,396,927 B2 | 7/2008 | Niddam-Hildesheim et al. | |
| 7,511,140 B2 | 3/2009 | Horbury et al. | |
| 7,582,759 B2 | 9/2009 | Niddam-Hildesheim et al. | |
| 2007/0037979 A1 | 2/2007 | Niddam-Hildesheim | |
| 2007/0099994 A1 | 5/2007 | Niddam-Hildesheim | |
| 2007/0167625 A1 | 7/2007 | Niddam-Hildesheim et al. | |
| 2007/0191318 A1 | 8/2007 | Kumar et al. | |
| 2007/0191436 A1 | 8/2007 | Niddam-Hildesheim | |
| 2007/0255060 A1 | 11/2007 | Okada | |
| 2008/0188504 A1 | 8/2008 | Casar et al. | |
| 2008/0234302 A1 | 9/2008 | Rafeeq et al. | |
| 2008/0255170 A1 | 10/2008 | Zlicar | |
| 2009/0036680 A1 | 2/2009 | Kumar et al. | |
| 2009/0111839 A1 | 4/2009 | Zlicar et al. | |
| 2009/0124803 A1* | 5/2009 | Deshpande | 544/322 |
| 2009/0187026 A1 | 7/2009 | Niddam-Hildesheim | |
| 2009/0209567 A1 | 8/2009 | Niddam-Hildesheim | |
| 2009/0215806 A1 | 8/2009 | Niddam-Hildesheim | |
| 2009/0240054 A1 | 9/2009 | Niddam-Hildesheim et al. | |

FOREIGN PATENT DOCUMENTS

| | | |
|---|---|---|
| WO | WO 00/49014 A1 | 2/2000 |
| WO | WO 03/097614 A2 | 11/2003 |
| WO | WO 2004/014872 A1 | 2/2004 |
| WO | WO 2004/052867 A1 | 6/2004 |
| WO | WO 2006/076845 A1 | 7/2006 |
| WO | WO 2006/100689 A1 | 9/2006 |
| WO | WO 2006/106526 A1 | 10/2006 |
| WO | WO 2007/000121 A1 | 1/2007 |
| WO | WO 2007/007119 A1 | 1/2007 |
| WO | WO 2007/099561 A1 | 9/2007 |
| WO | WO 2008/044243 A2 | 4/2008 |
| WO | WO 2009/019211 A1 | 2/2009 |
| WO | WO 2009/047576 A1 | 4/2009 |

OTHER PUBLICATIONS

Lynch et al., Tetrahedron Letters, 28(13), 1385-8 (1987).*
Baader et al., Tetrahedron Letters, 30(38), 5115-18 (1989).*
Patel et al., Journal of Organic Chemistry, 57(26), 7143-51 (1992).*
Nagasawa et al., Journal of Organic Chemistry 58(9), 2523-9 (1993).*
Suzuki et al., Bioorganic and Medicinal Chemistry Letters, 9(20), 2977-2982 (1999).*

* cited by examiner

*Primary Examiner* — James O. Wilson
*Assistant Examiner* — Alexander R Pagano
(74) *Attorney, Agent, or Firm* — Jay R Akhave; Patent Science LLC

(57) ABSTRACT

The present invention relates to an improved process for preparing Rosuvastatin calcium of Formula I.

(I)

11 Claims, No Drawings

PROCESS FOR PREPARING ROSUVASTATIN CALCIUM

This application is the National stage of International Application No. PCT/IB2007/003312, filed on Oct. 29, 2007, which claims benefit under U.S.C §119 to Indian patent application number 1994/CHE/2006 filed on Oct. 31, 2006, all of which are hereby expressly incorporated by reference into the present application.

FIELD OF THE INVENTION

The present invention relates to an improved process for preparing Rosuvastatin calcium of Formula I

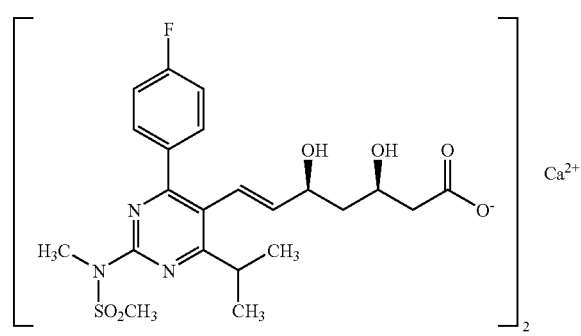

Formula I

BACKGROUND OF THE INVENTION

Rosuvastatin, which is an antihyperchlolesterolemic drug, is chemically known as (E)-7-[4-(4-fluorophenyl)-6-isopropyl-2-[methyl(methylsulfonyl)amino]pyrimidin-5-yl]-(3R,5S)-3,5-dihydroxyhept-6-enoic acid calcium (2:1) salt of Formula I.

Rosuvastatin was for the first time disclosed in U.S. Pat. No. 5,260,440. Rosuvastatin is being marketed under the proprietary name CRESTOR, as an oral tablet, for the treatment of hypercholesterolemia. In view of the importance of Rosuvastatin as a Lipid-lowering agent, several synthetic methods have been reported in the literature to prepare Rosuvastatin, some of which are as summarized below:

U.S. Pat. No. 5,260,440 discloses a process for preparing Rosuvastatin in examples. The process is as shown below:

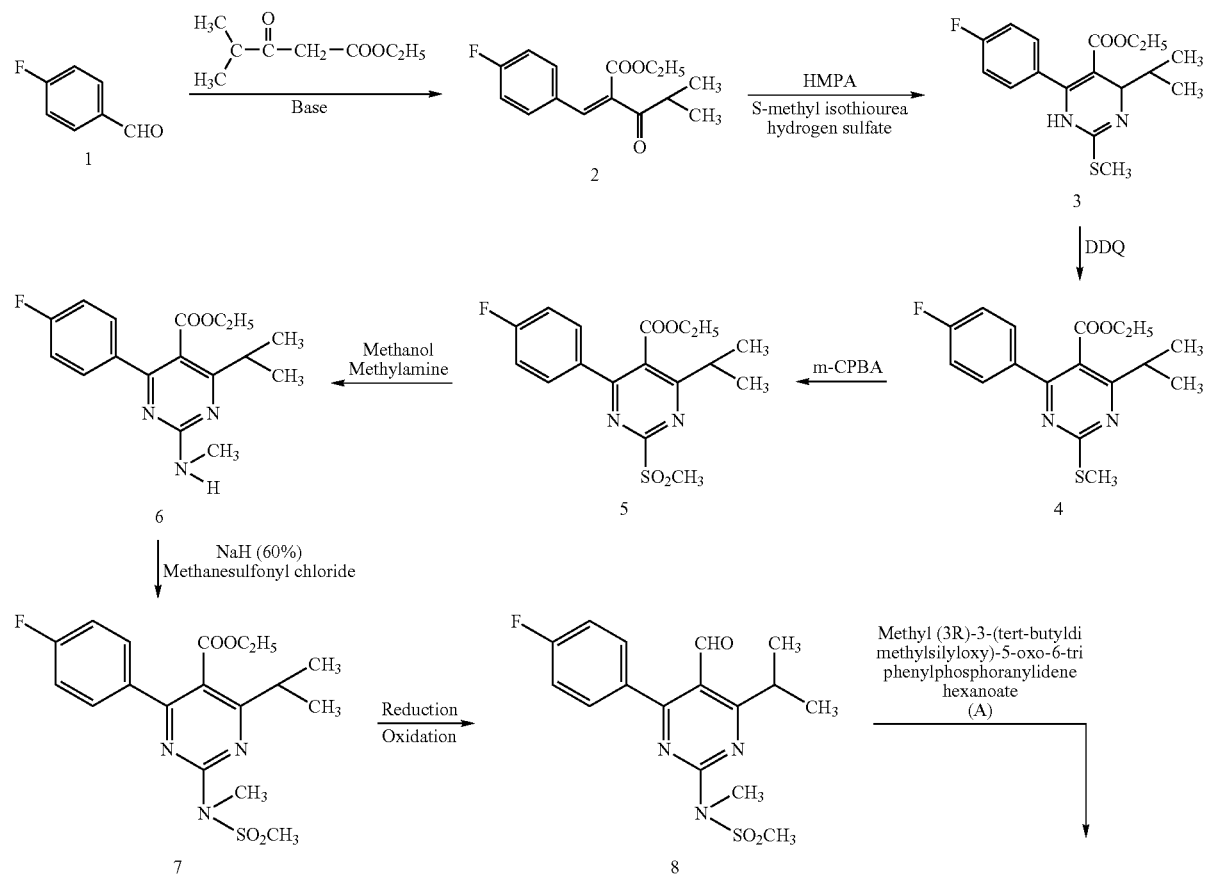

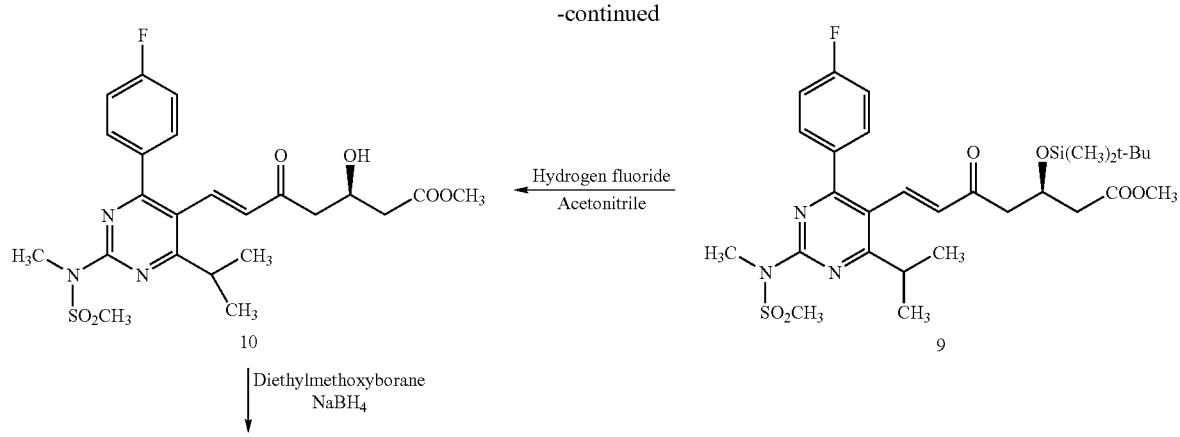

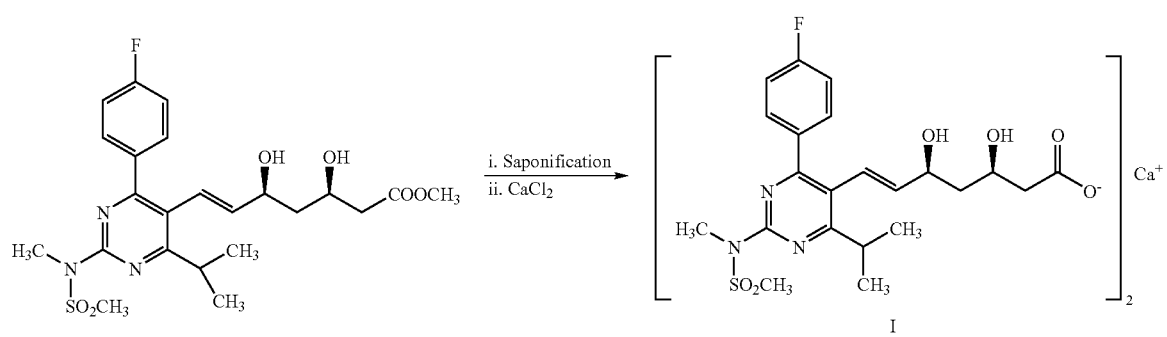

The difficulties in the above process are that the intermediate (A) is not obtained in pure form readily and its purification is tedious and overall yield is extremely low. Even when intermediate (A) is obtained in pure form, further condensation with intermediate (8) does not result in Rosuvastatin of right quality as the product contains unacceptable level of impurities and further the intermediates are obtained as liquids making it difficult to purify.

WO 2006/076845 A1 discloses a process to prepare Rosuvastatin, which comprises nitrilation of pyrimidine aldehyde (11) to give a cyano compound (12) followed by reduction to give 4-(4-fluorophenyl)-6-isopropyl-2-(N-methyl-N-mesylamino)pyrimidin-5-propenal (13) and then converted to Rosuvastatin. The process is as shown below:

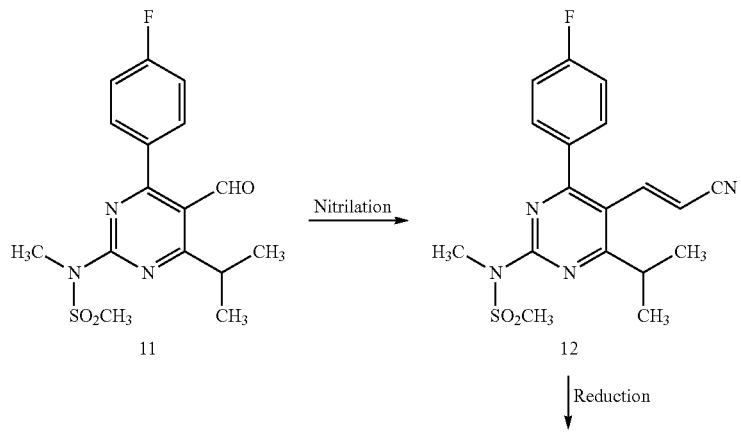

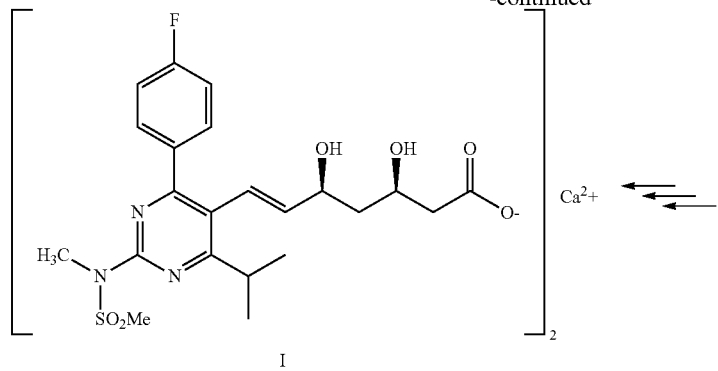
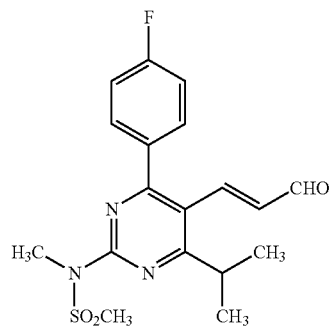

In this process, nitrilation is carried out using diethylcyanomethyl phosphate. The disadvantage of this process is that during conversion of cyano functionality into aldehyde, lots of impurities are formed along with unwanted cis-isomer, therefore the yield and purity of the product are poor.

WO 03/097614 A2 describes a modified procedure for the preparation of the starting material 4-(4-fluorophenyl)-6-isopropyl-2-(N-methyl-N-methylsulfonylamino)-5-pyrimidinecarboxaldehyde and further conversion to Rosuvastatin by condensing with methyl (3R)-3-[(tert-butyldimethylsilyl)oxy]-5-oxo-6-triphenylphosphoranylidene hexanoate. The condensed product was deprotected using methanesulfonic acid and subsequently converted to Rosuvastatin calcium (2:1) salt.

WO 2004/052867 A1 describes a process to prepare Rosuvastatin by condensing 1-cyano-(2S)-2-[(tert-butyldimethylsilyl)oxy]-4-oxo-5-triphenylphosphoranylidene pentane with 4-(4-fluorophenyl)-6-isopropyl-2-(N-methyl-N-methanesulfonylamino)-5-pyrimidinecarbaldehyde and subsequent deprotection of silyl group, reduction and hydrolysis.

WO 2000/049014 A1 discloses a novel chemical process for the manufacture of tert-butyl-(E)-(6-{2-[4-(4-fluorophenyl)-6-isopropyl-2-methyl(methylsulfonyl)amino]-pyrimidin-5-yl]vinyl}-(4R,6S)-2,2-dimethyl[1,3]dioxan-4-yl)acetate, which comprises reaction of diphenyl {4-(4-fluorophenyl)-6-isopropyl-2-[methyl-(methylsulfonyl)amino]pyrimidin-5-yl-methyl}phosphineoxide with tert-butyl 2-[(4R,6S)-6-formyl-2,2-dimethyl-1,3-dioxan-4-yl]acetate and its further conversion to Rosuvastatin.

WO 2004/014872 A1 describes a process for the manufacture of Rosuvastatin calcium (2:1) salt which comprises mixing a solution of calcium chloride with a solution of water soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid. This process for the preparation of Rosuvastatin employs the use of phosphorane side chain; the preparation of side chain requires eight synthetic steps and involves expensive reagents. The process is both uneconomical and time consuming, hence not appropriate for commercial scale operation.

WO 2006/100689 A1 discloses a process for preparation of Rosuvastatin as shown below:

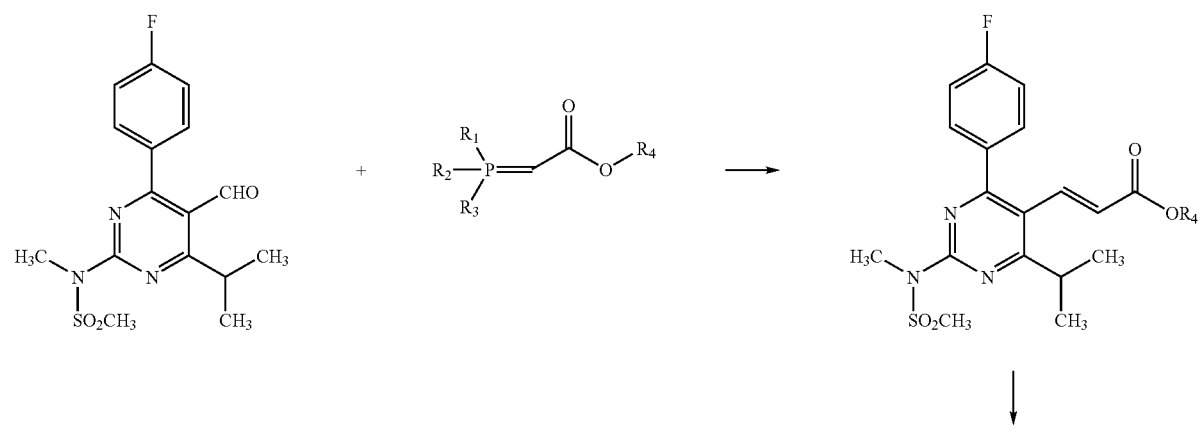

-continued
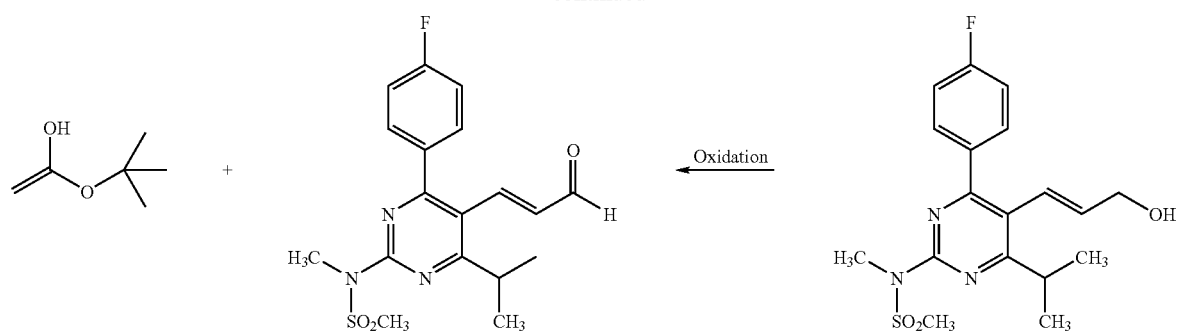
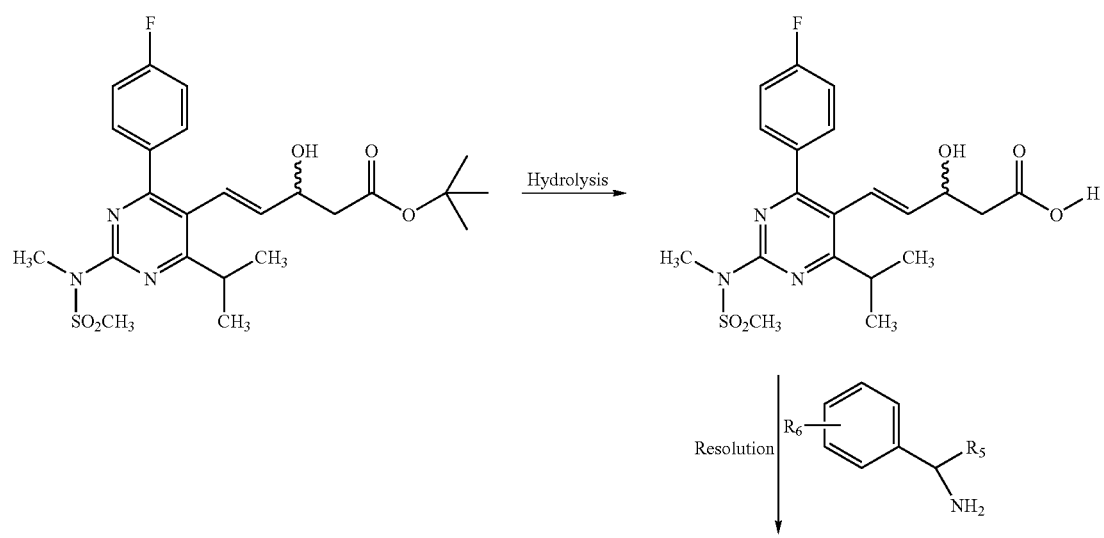
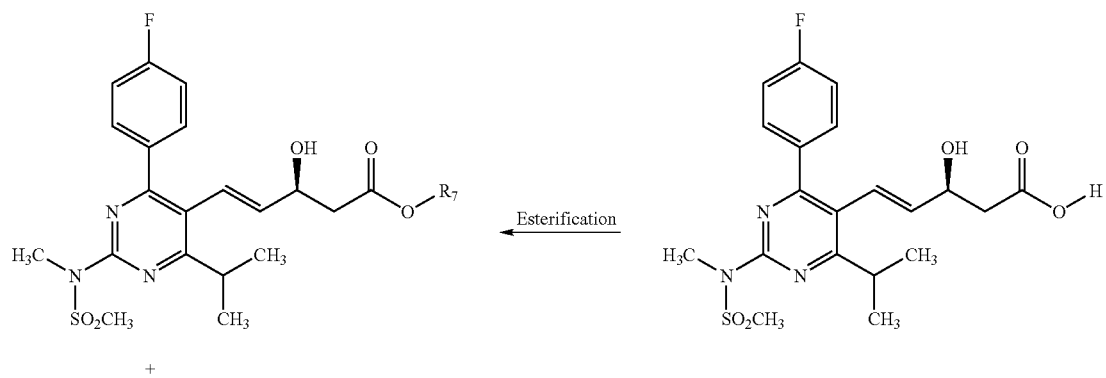

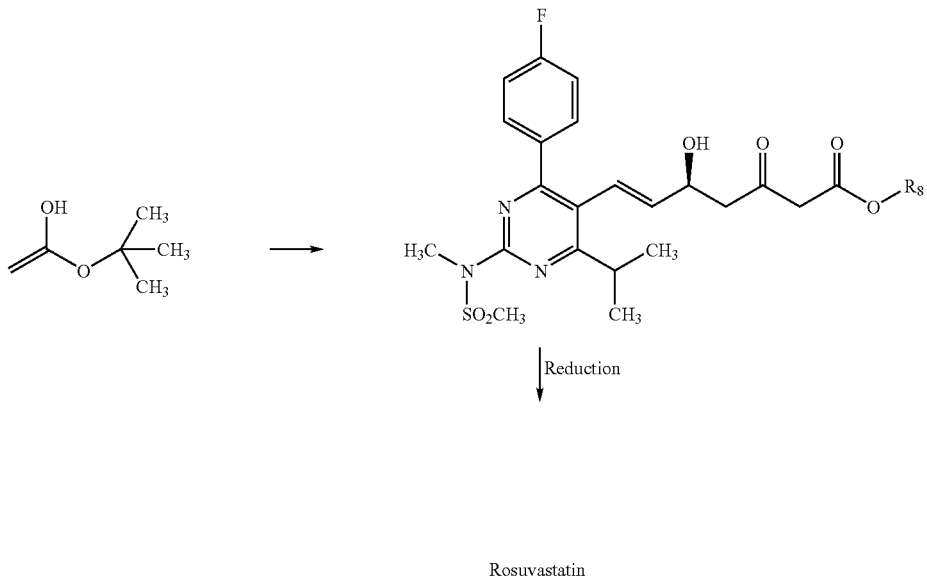

Rosuvastatin

In the above scheme $R_1$, $R_2$, $R_3$ represent substituted or unsubstituted phenyl and $R_4$ represents an aliphatic residue selected from $C_1$-$C_4$ alkyl, $R_5$ represents $C_1$-$C_4$ alkyl which is optionally substituted by hydroxyl, $R_6$ represents hydrogen, halogen, $C_1$-$C_4$ alkyl or $C_1$-$C_4$ alkoxy, $R_7$ represents aliphatic residue, $R_8$ represents $C_1$-$C_4$ alkyl.

WO 2006/106526 A1 describes the preparation of Rosuvastatin as shown below:

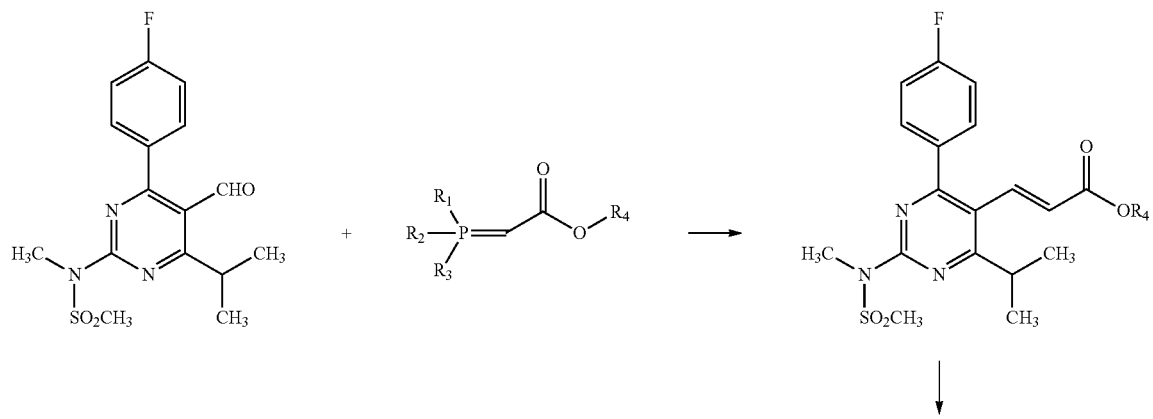

11 -continued 12
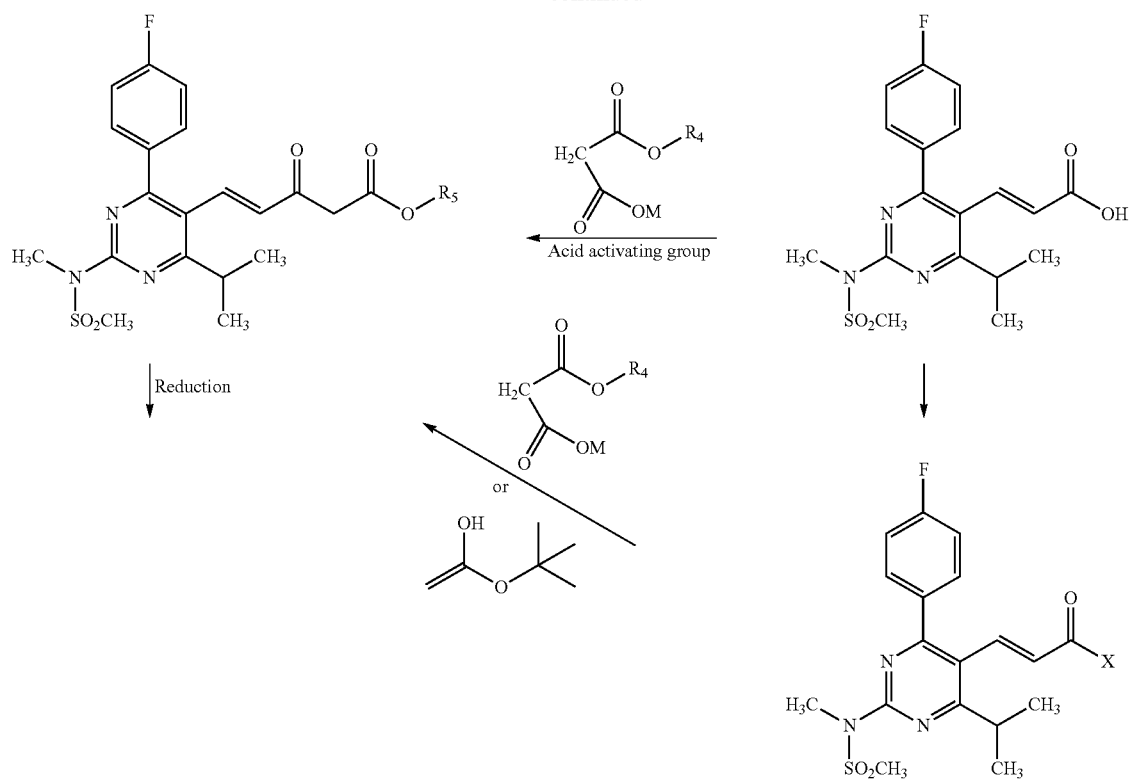
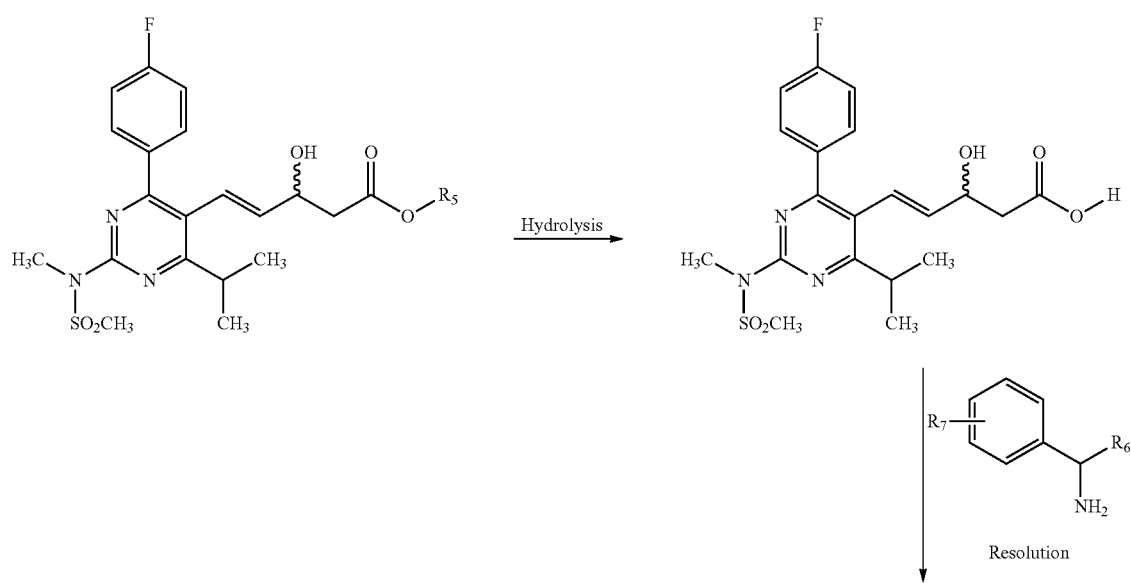

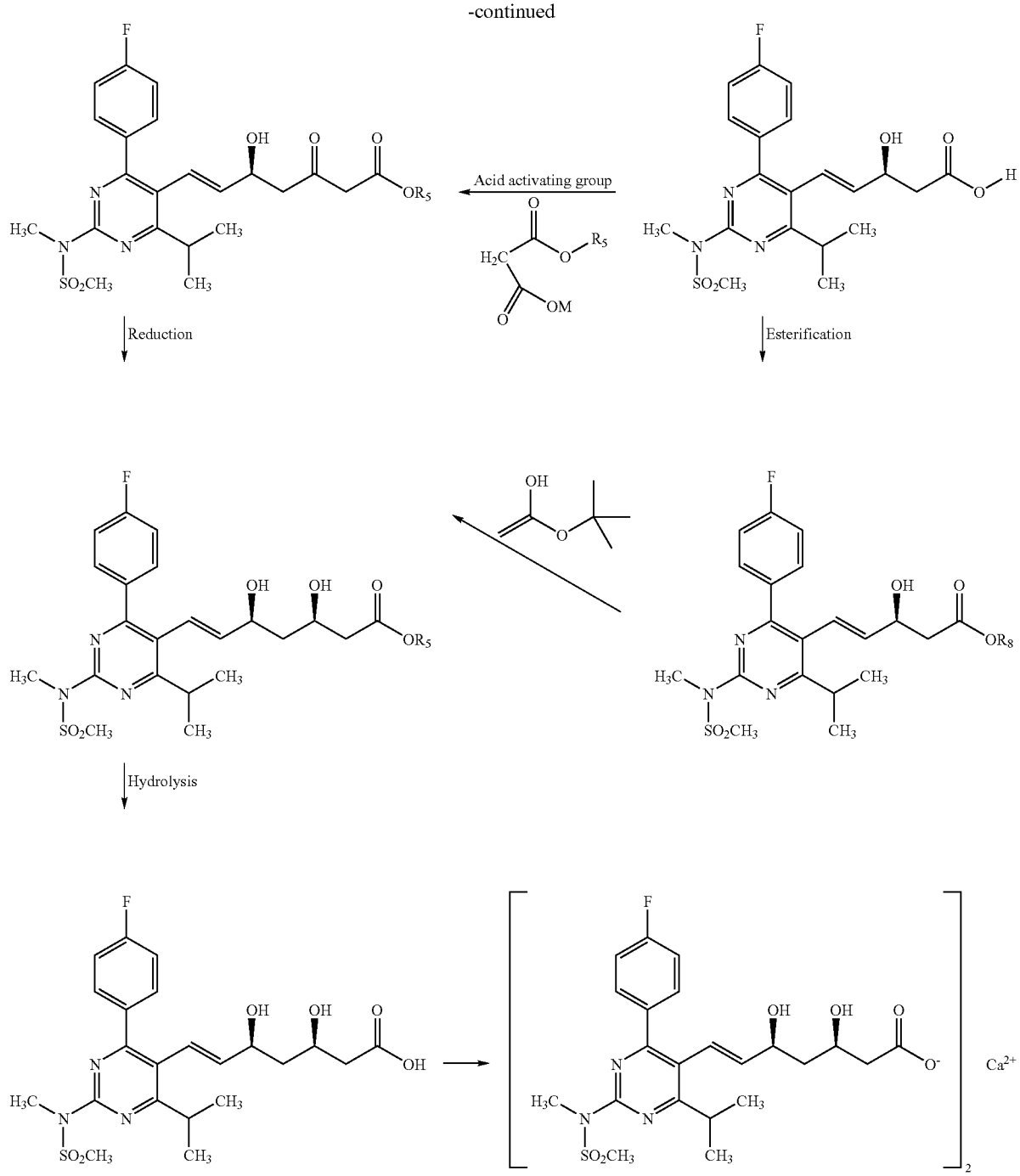

In the above mentioned scheme $R_1$, $R_2$, $R_3$ are substituted or unsubstituted phenyl and $R_4$ is an aliphatic residue selected from $C_1$-$C_4$ alkyl, $R_5$ represents $C_1$-$C_4$ alkyl, M is an alkali metal salt, X represents a halogen, $R_6$ represents $C_1$-$C_4$ alkyl which is optionally substituted by hydroxyl, $R_7$ represents hydrogen, halogen, $C_1$-$C_4$ alkyl or $C_1$-$C_4$ alkoxy, $R_8$ is an aliphatic residue selected from $C_1$-$C_4$ alkyl.

We have now found an improved process to prepare (+)-(3R,5S)-7-[4-(4-fluorophenyl)-6-isopropyl-2-(N-methyl-N-methylsulfonylamino)pyrimidin-5-yl]-3,5-dihydroxy-6E-heptenoic acid calcium salt of Formula I that is cost effective and industrially feasible.

Objective

The main objective of the present invention is to provide an improved process for preparing (+)-(3R,5S)-7-[4-(4-fluorophenyl)-6-isopropyl-2-(N-methyl-N-methyl-sulfonylamino)pyrimidin-5-yl]-3,5-dihydroxy-6E-heptenoic acid calcium salt of Formula I.

Yet another objective of the present invention is to provide an improved process for preparing (+)-(3R,5S)-7-[4-(4-fluorophenyl)-6-isopropyl-2-(N-methyl-N-methyl-sulfonylamino)pyrimidin-5-yl]-3,5-dihydroxy-6E-heptenoic acid calcium salt of Formula I, which is simple, industrially applicable and economically viable.

SUMMARY OF THE INVENTION

The present invention relates to an improved process for preparing Rosuvastatin calcium of Formula I

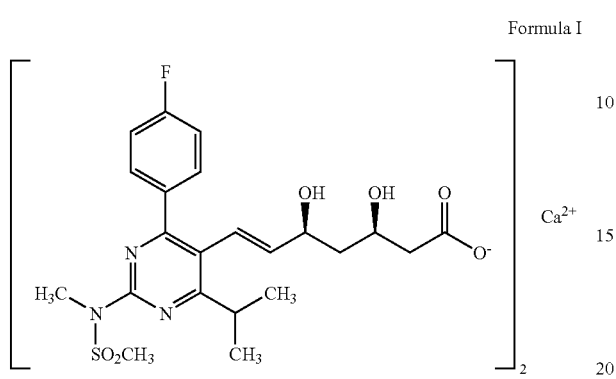

Formula I which comprises:

a) reacting (2E)-3-[4-(4-fluorophenyl)-6-isopropyl-2-(N-methyl-N-methanesulfonylamino)pyrimidin-5-yl]-propenal of Formula II,

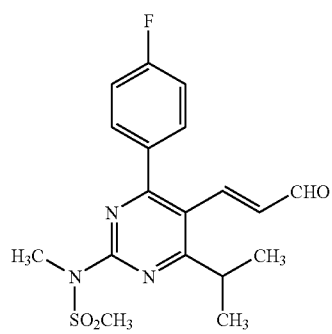

Formula II with a compound of Formula III a or III b

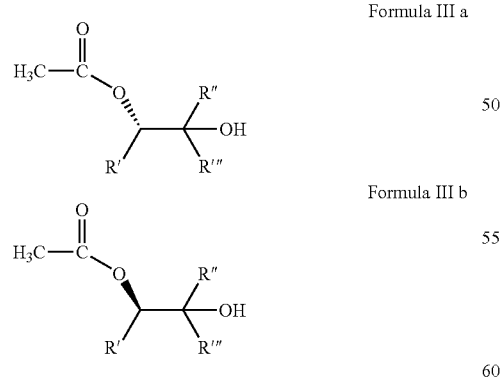

Formula III a

Formula III b wherein R', R" and R'" represent alkyl, aralkyl, cycloalkyl, substituted cycloalkyl, phenyl, substituted phenyl, napthyl, substituted napthyl and heterocyclic residue, in the presence of a base and an organic solvent to produce a diastereomeric mixture of compound of Formula IV a or IV b

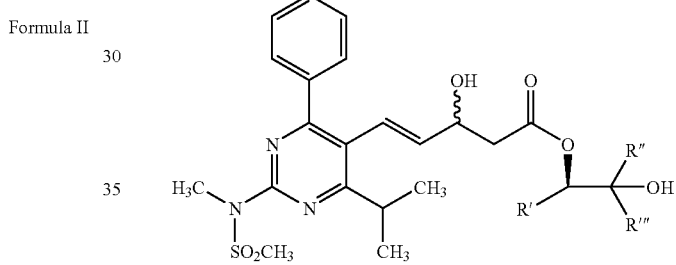

Formula IV a

Formula IV b wherein R', R" and R'" are defined as above, b) converting the diastereomeric mixture of compound of Formula IV a or IV b to a compound of Formula V

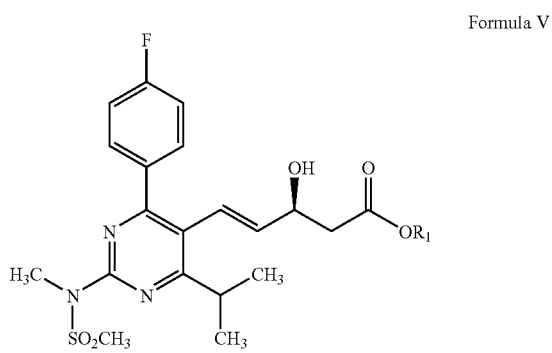

Formula V wherein $R_1$ represents $C_{1-5}$ alkyl, c) protecting the compound of Formula V with a suitable hydroxy protecting group to give a compound of Formula VI Formula VI

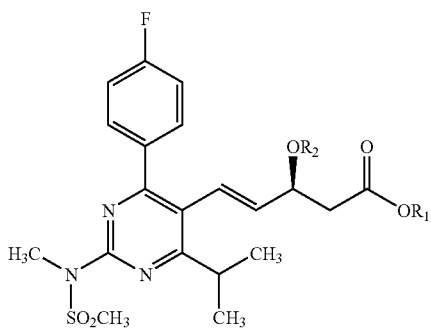

wherein R₂ represents a hydroxy protecting group and R₁ is defined as above, d) reacting compound of Formula VI with an ester of acetic acid of Formula of H₃C—CO—OR₃ in presence of a base to give compound of Formula VII Formula VII

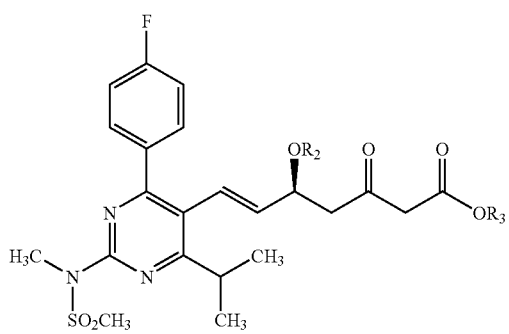

wherein R₂ is defined as above and R₃ represents $C_{1-5}$ alkyl, phenyl, substituted phenyl, aralkyl, e) selectively deprotecting the compound of Formula VII to give compound of Formula VIII Formula VIII

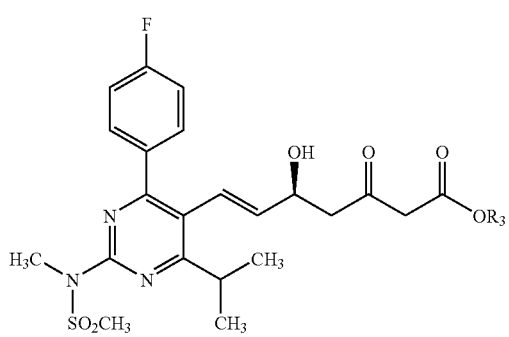

wherein R₃ is as defined above, f) selectively reducing the compound of Formula VIII with alkali metal borohydride in presence of chelating agent to give the desired compound of Formula IX Formula IX

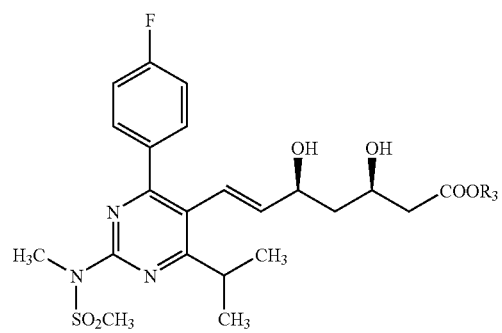

wherein R₃ represents $C_{1-5}$ alkyl, aralkyl, phenyl and substituted phenyl, and subsequently converting the compound of Formula IX to Rosuvastatin calcium of Formula I.

DETAILED DESCRIPTION OF THE INVENTION

The main aspect of the present invention is to provide a novel process for the preparation of Rosuvastatin in higher yield.

The compound of Formula II is condensed with compound of Formula III a or III b in presence of base. This condensation is carried out in a single organic solvent like ether, tetrahydrofuran, hydrocarbon solvents like heptane, hexane or mixture thereof. The preferred solvents are tetrahydrofuran and hexane. The base used in the above condensation is selected from n-butyllithium, lithium hexamethyldisilazane, sodium hexamethyldisilazane, lithium diisopropylamine, etc more preferably lithium hexamethyldisilazine. The condensation reaction is carried out at a temperature ranging from −78° C. to +20° C. After completion, the reaction is quenched with 5 N HCl and extracted with an organic solvent to give a diasteromeric mixture of compounds of Formula IV a or Formula IV b. The mixture of compound of Formula IV a or Formula IV b which contains predominantly diastereomers IV c or IV d with 3(S) configuration is crystallized to give diastereomerically pure IV c or IV d with the following structures Formula IV c

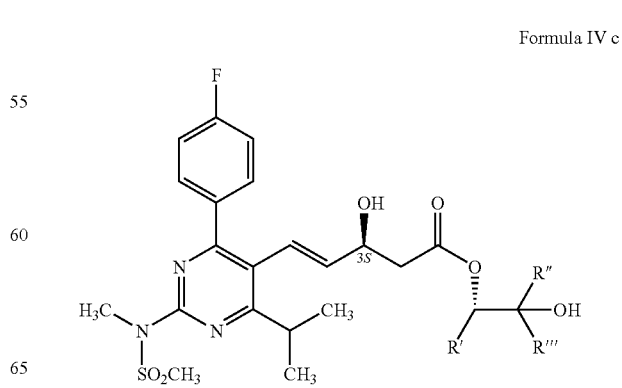

Formula IV d

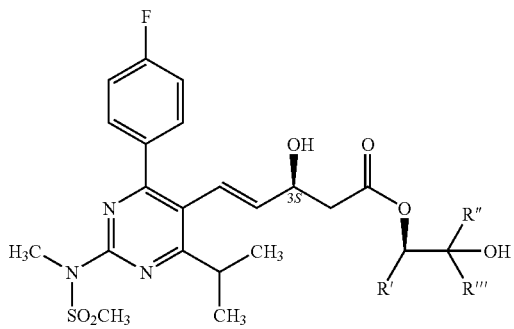

The purification of the diastereomeric mixture of compounds of Formula IV a or Formula IV b is achieved in hexane, ethyl acetate, butyl acetate, toluene, MTBE, acetone, acetonitrile, IPE and mixtures thereof. The compound of Formula IV c or IVd is converted to enatiomerically pure compound of Formula V by treating the compound of Formula IV c or Formula IV d with a lower alcohol such as methanol, ethanol in the presence of a base such as potassium carbonate, sodium carbonate and the like.

Alternatively, the mixture of compound of Formula IV a or IV b is first hydrolyzed to its corresponding acid of the following Formula X Formula X

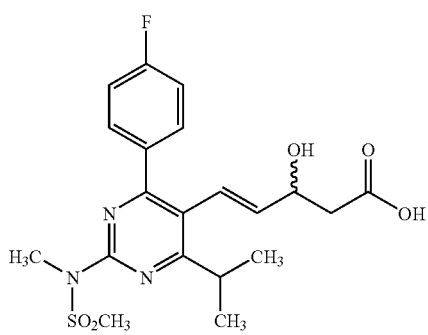

which is then resolved using optically pure precipitating agents, for example (+) or (−) phenylalkylamine or substituted phenylalkylamine, Ephedrine (+) (−), 1-amino-1-butanol (+) (−), Quinine (−), Quinidine (+), Cinchonidine (+), Brucine (−), Dehydroabietylamine (+), preferably (R)-1-phenylethylamine in a suitable organic solvent to get enantiomerically pure compound of Formula XI. The organic solvent is selected from acetonitrile, tetrahydrofuran, ethyl acetate, methanol, ethanol, isopropyl alcohol or a mixture of organic solvent and water.

Formula XI

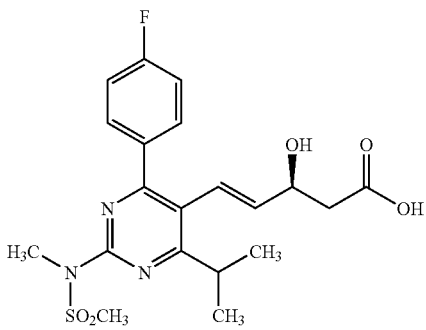

The compound of Formula XI is esterified to get enantiomerically pure compound of Formula V.

The enantiomerically pure compound of Formula V is protected with a suitable hydroxy protecting group like tertiary butyl dimethylsilyl, dihydropyran etc. The protection is carried out in an organic solvent selected from toluene, N,N'-Dimethylformamide, tetrahydrofuran, dichloromethane etc., with or without an acid catalyst. The acid catalyst can be chosen from pyridinium p-toluene sulfonate, p-toluenesulfonic acid, acetic acid etc. The hydroxy protection is carried out at a temperature ranging from 0-50° C. preferably at 0-30° C. The compound of Formula VI is isolated by washing the organic layer with water and evaporating the solvent.

The compound of Formula VI is treated with anion generated from acetates like ethyl acetate, phenyl acetate, methyl acetate, t-butyl acetate in an organic solvent. For anion generation several bases can be used like n-butyllithium, lithium diisopropylethylamine, lithium hexamethyldisilazane, sodium hexamethyldisilazane, or inorganic bases in combination with phase transfer catalyst, more preferably lithium diisopropylethylamine is used. The solvent employed is selected from tetrahydrofuran, methyl tert-butyl ether, isopropyl ether, hexane, heptane or mixture thereof. The reaction is carried out at temperature −78° C. to 0° C. The reaction mixture is quenched in 1N HCl and extracted with a suitable organic solvent to produce compound of Formula VII.

The compound of Formula VII is deprotected using acid catalysts like p-toluenesulfonic acid, acetic acid, hydrochloric acid, hydrofluoric acid etc., or salts such as sodium fluoride, potassium fluoride. The preferred acid catalyst employed is p-toluenesulfonic acid to give hydroxy compound of Formula VIII.

The compound of Formula VIII is stereoselectively reduced with metal borohydrides in presence of chelating agent like trialkylboranes or boranates like dialkyl alkoxy boranes. This stereoselective reduction is carried out in one or more organic solvents with sodium borohydride, potassium borohydride, calcium borohydride and chelating agent at low temperatures. The reduction is carried out in one or more organic solvents at −10 to −80° C. After completion of the reaction, excess borohydride is destroyed by acetic acid or high bases like sodium bicarbonate, potassium bicarbonate and resulting compound of Formula IX is extracted into organic solvent.

The compound of Formula IX is further converted to Rosuvastatin by following known methods reported in literature. The Rosuvastatin obtained by the process of the present invention is converted into pharmaceutically acceptable salts such as sodium, calcium more preferably calcium salt.

The process for preparing (2E)-3-[4-(4-fluorophenyl)-6-isopropyl-2-(N-methyl-N-methylsulfonylamino)pyrimidin-5-yl]-propenal of Formula II Formula II

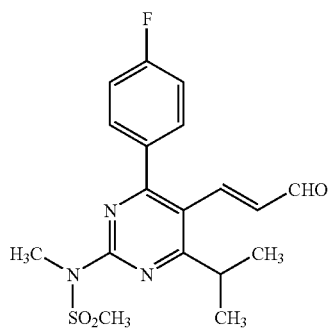

which comprises,
a) treating 4-(4-fluorophenyl)-6-isopropyl-2-(N-methyl-N-methylsulfonylamino)pyrimidin-5-yl]-carboxaldehyde of Formula XII, Formula XII

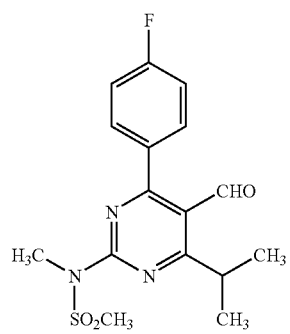

with a phosphorous compound of Formula XIII,

Formula XIII

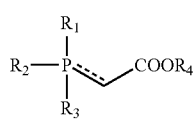

wherein $R_1$ represents (=O), $C_{1-4}$ alkyl, aralkyl, phenyl, substituted phenyl, "--" represents an optional bond with a proviso that when represents ($R_1$=O), "--" is not a bond and where $R_1$ represents $C_{1-4}$alkyl, phenyl, substituted phenyl then "--" is a bond, $R_2$ represents $OR_5$, $C_{1-4}$ alkyl, aralkyl, phenyl, substituted phenyl; $R_3$ represents $OR_6$, $C_{1-4}$ alkyl, aralkyl, phenyl, substituted phenyl; $R_4$, $R_5$ and $R_6$ groups are selected from $C_{1-4}$ alkyl, aralkyl, phenyl, substituted phenyl; optionally in the presence of a base and organic solvent to produce a substituted (2E)-3-[4-(4-fluorophenyl)-6-isopropyl-2-(N-methyl-N-methylsulfonylamino)pyrimidin-5-yl]-1-propenoate of Formula XIV, Formula XIV

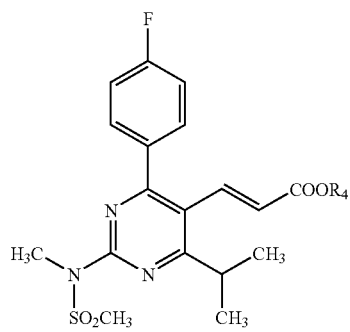

wherein $R_4$ represents $C_{1-4}$ alkyl, phenyl, substituted phenyl, reducing the compound of Formula XIV to give a (2E)-3-[4-(4-fluorophenyl)-6-isopropyl-2-(N-methyl-N-methylsulfonylamino)pyrimidin-5-yl]propen-1-ol of Formula XV, Formula XV

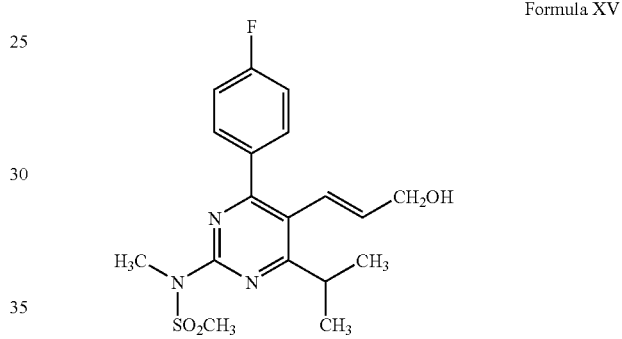

c) oxidizing the compound of Formula XV to give (2E)-3-[4-(4-fluorophenyl)-6-isopropyl-2-(N-methyl-N-methylsulfonylamino)pyrimidin-5-yl]-propenal of Formula II.

The compound of Formula XII is reacted with a phosphorous compound of Formula XIII optionally in the presence of a base such as organic or inorganic base and a solvent selected from acetonitrile, dichloromethane, tetrahydrofuran, methanol, ethanol, isopropyl alcohol and mixtures thereof, at temperature ranging from 20 to 90° C., preferably 40-80° C. for 8 h to yield a compound of Formula XIV. The organic base is selected from sodium methoxide, lithium diisopropylamide, n-butyllithium, lithium hexamethyldisilazane, sodium hexamethyldisilazane. The inorganic base is selected from sodium hydride, potassium hydride, sodium hydroxide, potassium carbonate. The obtained compound of Formula XIV is reduced using a reducing agent such as DIBAL, Vitride, LAH etc., in an organic solvent such as toluene, tetrahydrofuran at −70° to −80° C., preferably at −78° C. to yield a compound of Formula XV. The compound of Formula XV is oxidized using an oxidizing agent such as pyridiniumdichromate (PDC), pyridinium chlorochromate (PCC), manganese dioxide ($MnO_2$), 2,2,6,6-tetramethylpiperidine N-oxide (TEMPO), and tetrapropylammoniumperrutheniate (TPAP), sodium hypochlorite (NaOCl)/TEMPO, N-methylmorpholine N-oxide (NMO) and the like at the temperature ranging from 0 to 100° C. preferably at 0 to 20° C. to yield compound of Formula II.

The invention is illustrated with the following examples, which are provided by way of illustration only and should not be construed to limit the scope of the invention.

EXAMPLE 1

Preparation of 3-[4-(4-Fluorophenyl)-6-Isopropyl-2-(N-Methyl-N-Methylsulfonylamino)Pyrimidin-5-yl]-(2E)-Propenal Step I:

Preparation of Methyl (2E)-3-[4-(4-fluorophenyl)-6-isopropyl-2-(N-methyl-N-methylsulfonylamino) pyrimidin-5-yl]propenoate 4-(4-Fluorophenyl)-6-isopropyl-2-(N-methyl-N-methylsulfonylamino)pyrimidine-5-ylcarboxaldehyde (5 g) was dissolved in acetonitrile (25 ml) and to the resulting solution Methyl (triphenylphosphoranylidene)acetate (5.23 g) was added at room temperature. The reaction mixture was stirred at 80-81° C. for 8 h for completion. Thereafter, acetonitrile was distilled off under reduced pressure to give crude mass, which was crystallized from isopropyl alcohol to yield pure methyl (2E)-3-[4-(4-fluorophenyl)-6-isopropyl-2-(N-methyl-N-methylsulfonylamino)pyrimidin-5-yl]propenoate.

Yield: 5.4 g (96.0%)

$^1$H NMR (300 MHz) in CDCl$_3$; δ(ppm): 1.32 (d, J=6 Hz, 6H), 3.34-3.43 (m, 1H), 3.52 (s, 3H), 3.59 (s, 3H), 3.77 (s, 3H), 5.86 (d, J=15 Hz, 1H), 7.10-7.27 (n, 2H), 7.58-7.63 (m, 2H), 7.74 (d, J=15 Hz, 1H)

Step II:

Preparation of (2E)-3-[4-(4-Fluorophenyl)-6-isopropyl-2-(N-methyl-N-methylsulfonylamino)pyrimidin-5-yl]-propen-1-ol Methyl (2E)-3-[4-(4-fluorophenyl)-6-isopropyl-2-(N-methyl-N-methylsulfonyl-amino)pyrimidin-5-yl]-1-propenoate (5.4 g) obtained in step I above was dissolved in toluene (30 ml) and the resulting solution was cooled to −78° C. To this solution, diisobutylaluminium hydride (20% solution in toluene, 45.2 ml) was added and the reaction mass was stirred at −70° C. for 15 min. Thereafter, reaction mass was poured into aqueous hydrochloric acid (1N, 30 ml). The organic layer was separated and washed with water (20 ml). The solvent was distilled under reduced pressure to yield pure (2E)-3-[4-(4-fluorophenyl)-6-isopropyl-2-(N-methyl-N-methylsulfonylamino)pyrimidin-5-yl]-propen-1-ol.

Yield: 5.1 g (98.0%)

$^1$H NMR (300 MHz) in CDCl$_3$; δ(ppm): 1.28 (d, J=6.9 Hz, 6H), 3.38-3.42 (m, 1H), 3.53 (s, 3H), 3.59 (s, 3H), 4.22 (brs, 2H), 5.67 (dt, J=16.0 & 5 Hz), 6.6 (d, J=16.0 Hz, 1H), 7.08-7.14 (m, 2H), 7.64-7.69 (m, 2H)

Step III:

Preparation of (2E)-3-[4-(4-Fluorophenyl)-6-isopropyl-2-(N-methyl-N-methylsulfonylamino)pyrimidin-5-yl]-propenal Methyl (2E)-3-[4-(4-fluorophenyl)-6-isopropyl-2-(N-methyl-N-methylsulfonyl-amino)pyrimidin-5-yl]propen-1-ol (5.1 g) was added to molecular sieves (1 g) in dichloromethane (50 ml) and stirred for 15 min at room temperature. A solution of pyridinium dichromate (6.07 g) in dichloromethane (20 ml) was added to the above reaction mixture and continued stirring for 5 h at room temperature. After completion of the reaction, the reaction mass was filtered through a column of silica gel (230-400 mesh) and the eluate was distilled under reduced pressure to yield a semi-solid compound, which was crystallized from Hexane : Ethyl acetate (95 : 5 v/v) to yield (2E)-3-[4-(4-fluorophenyl)-6-isopropyl-2-(N-methyl-N-methylsulfonylamino)pyrimidin-5-yl]-propenal.

Yield: 5.0 g (98.5%)

$^1$H NMR (300 MHz) in CDCl$_3$; δ(ppm): 1.36 (d, J=5 Hz, 6H), 3.38-3.42 (m, 1H), 3.56 (s, 3H), 3.59 (s, 3H), 6.19-6.27 (dd, J=16.5 & 7.5 Hz), 7.13-7.18 (m, 2H), 7.55 (d, J=16.5 Hz, 1H), 7.60-7.63 (m, 2H), 9.63 (d, J=7.5 Hz, 1H)

EXAMPLE 2

Preparation of (3S)-5-[4-(4-Fluorophenyl)-6-Isopropyl-2-(N-Methyl-N-Methylsulfonylamino)Pyrimidin-5-yl]-3-Hydroxy-4-Pentenoic Acid (1S)-2-Hydroxy-1,2,2-Triphenylethyl Ester A mixture of hexamethyldisilazane (33.5 ml, 0.15 mol) and tetrahydrofuran (50 ml) was cooled to −10° C. under nitrogen atmosphere. n-Butyllithium (3.92 ml, 14% in Hexanes) was added over a period of 20 min (Exothermic), keeping the temperature below 0° C. The reaction mixture was stirred at 0 to −5° C. for 15 min and then cooled to −35° C. before adding 2-(S)-acetoxy-1,1,2-triphenylethanol (4.84 g, 0.014 mol) over a period of 5 min. The temperature of the reaction mixture was allowed to go up to −15° C. and stirred for 45 min. The resulting homogeneous yellow solution was cooled to −78° C. and a solution of (2E)-3-[4-(4-fluorophenyl-6-isopropyl-2-(N-methyl-N-methylsulfonylamino)pyrimidin-5-yl]-propenal (5 g, 0.013 mol) in tetrahydrofuran (20 ml) was added over a period of 30 min maintaining the temperature at −75 to −78° C. The reaction mixture was stirred for 40 min at −78° C. and then slowly raised the temperature to 0° C. over a period of 20 min. The reaction mass was quenched by adding aqueous hydrochloric acid (5N, 30 ml). The organic layer was separated and the aqueous layer was extracted with ethyl acetate (50 ml). The combined organic extracts were washed with saturated sodium chloride solution (50 ml) and evaporated to get a solid mass. The product obtained from the above process was crystallized from hexane : ethyl acetate (9:1 v/v, 50 ml).

Yield: 9.0 g $^1$H NMR (300 MHz, CDCl$_3$): 1.26 (d, J=6 Hz, 6H), 2.37 (d, J=6 Hz, 2H), 2.70 (brs,1H), 2.84 (s, 1H), 3.30-3.35 (m, 1H), 3.53 (s, 3H),3.59 (s, 3H), 4.44 (brs, 1H), 5.37 (dd, J=16, 5 Hz, 1H), 6.6 (d, J=16 Hz, 1H), 6.7 (s, 1H), 7.05-7.19 (m, 15H), 7.28-7.38(m,2H), 7.58-7.59 (m, 2H).

EXAMPLE 3

Preparation of (3S)-5-[4-(4-Fluorophenyl)-6-Isopropyl-2-(N-Methyl-N-Methylsulfonylamino)Pyrimidin-5-yl]-3-Hydroxy-(4E)Pentenoic Acid Methyl Ester The product obtained in example 2 was dissolved in methanol and added anhydrous potassium carbonate (4 g). The mixture was stirred at room temperature for 3 h and methanol was distilled out from the reaction below 40° C. under reduced pressure. Water (50 ml) was added to the resulting residue and extracted with methylene chloride (50 ml). The methylene chloride layer was separated, washed with water (50 ml), dried over sodium sulfate and evaporated to dryness to obtain a viscous liquid. The product was purified by column chromatography using silica gel and hexane: ethyl acetate (80:20 v/v)

Yield: 5.5 g.

$^1$H NMR (300 MHz, CDCl$_3$): 1.26 (d, J=6 Hz, 6H), 2.41-2.47 (m, 2H), 3.10 (brs, OH), 3.31-3.36 (m, 1H), 3.52 (s, 3H), 3.57 (s, 3H), 3.70 (s, 3H), 4.52 (brs, 1H), 5.44-5.51 (dd, J=15, 6 Hz, 1H), 5.66 (d, J=15 Hz, 1H), 7.0-7.1 (m, 2H), 7.6-7.65 (m, 2H).

EXAMPLE 4

Preparation of (3RS)-5-[4-(4-Fluorophenyl)-6-Isopropyl-2-(N-Methyl-N-Methylsulfonylamino)Pyrimidin-5-yl]-3-(Tetrahydropyranyloxy]-(4E)-Pentenoic Acid Methylester The product of example 3 (5.5 g, 0.012 mol) was dissolved in methylene chloride (55 ml) and pyridinium-p-toluenesulfonate was added (0.55 g) at 25° C. followed by 3,4-dihydro-2H-pyran (1.34 ml, 0.014 mol). The reaction mass was stirred at room temperature for 24 h and added water (20 ml). The methylene chloride layer was separated, washed with water (20 ml), dried over sodium sulfate and evaporated under reduced pressure at below 40° C. to obtain the product as an oily mass, which was used in the subsequent reaction without further purification.

Yield: 6.5 g

EXAMPLE 5

Preparation of (5S)-7-[4-(4-Fluorophenyl)-6-Isopropyl-2-(N-Methyl-N-Methylsulfonylamino)Pyrimidin-5-yl]-5-(Tetrahydropyranyloxy)-3-Oxo-(6E)-Heptenoic Acid Tert-Butyl Ester A mixture of diisopropylamine (8.5 ml, 0.06 mol) and tetrahydrofuran (35 ml) was cooled to −10° C. and added n-butyllithium (18.8 ml, 14% solution in hexanes) slowly over a period of 15 min, keeping the temperature below 0° C. The mixture was stirred for 30 min, keeping the temperature between 0 to −5° C. Thereafter, the mixture was cooled to −78° C. and added tert-butyl acetate (1.8 ml, 0.013 mol) slowly over a period of 30 min, maintaining the temperature below −75° C. The reaction mass was stirred for 30 min, keeping the temperature between −75 to −78° C. The product of example 4 (6.5 g, 0.012 mol) was dissolved in tetrahydrofuran (20 ml) and added to the reaction mass slowly over a period of 20 min at −78° C. The reaction mass was stirred at −78° C. for 1 h and quenched by slow addition of 1N aqueous hydrochloric acid (10 ml). The organic layer was separated and the aqueous layer was extracted with ethyl acetate. The combined organic layer was washed with water (20 ml), dried over anhydrous sodium sulfate and evaporated to get the product as an oily mass and used as such in the next step.

Yield: 7 g

EXAMPLE 6

Preparation of (5S)-7-[4-(4-Fluorophenyl)-6-Isopropyl-2-(N-Methyl-N-Methylsulfonylamino)Pyrimidin-5-yl]-5-(Hydroxy)-3-Oxo-(6E)-Heptenoic Acid Tert.Butyl Ester The product obtained as per the procedure of example 4 (7.0 g, 0.01 mol) was dissolved in isopropyl alcohol (28 ml) and p-toluenesulfonic acid monohydrate (0.28 g, 0.0014 mol) was added to it. The mixture was stirred at room temperature for 24 h. After completion of the reaction, solvent was evaporated under reduced pressure at below 40° C. and water (20 ml) was added to it. The product was extracted using dichloromethane (35 ml) and washed the organic phase with water (20 ml). The organic layer was dried over sodium sulfate and evaporated the solvent to obtain the product Yield: 4.8 g, 80%

$^1$H NMR (300 MHz, CDCl$_3$): 1.29 (s, 9H), 1.46 (d, J=6 Hz, 6H), 2.34-2.67 (m, 4H), 3.30-3.37 (m, 1H), 3.53 (s, 3H), 3.59 (s, 3H), 3.72 (s, 1H), 4.63 (brs, 1H), 5.44-5.53 (m, 1H), 6.69 (d, J=15 Hz, 1H), 7.09-7.28 (m, 2H), 7.63-7.65 (m, 2H)

EXAMPLE 7

Preparation of t-Butyl-(6E)-7-{4-(4-Fluorophenyl)-6-Isopropyl-2-[N-Methyl-N-Methylsulfonylamino] Pyrimidin-5-yl}-(3R,5S)-3,5-Dihydroxy Heptenoate t-Butyl-(6E)-7-{4-(4-fluorophenyl)-6-isopropyl-2-[N-methyl-N-methylsulfonyl-amino]pyrimidin-5-yl}-(5S)-5-hydroxy-3-oxo heptenoate (2 g, 0.003 mol) was dissolved in tetrahydrofuran (54 ml) and methanol (14 ml) at 25-30° C. under nitrogen atmosphere. The mixture was cooled to −78° C. and diethylmethoxy borane (1 ml, 48% solution in tetrahydrofuran, 0.004 mol) was added to it drop wise at −78° C. over a period of 10 min. The mixture was stirred at −75° C. to −78° C. for one hour and sodium borohydride (0.14 gm, 0.003 mol) was added to it slowly over a period of 15 min. It was stirred for 2 h at -75° C. to −78° C. and quenched by adding acetic acid (2 ml) at −78° C. Saturated aqueous sodium bicarbonate solution (50 ml) was added to it and stirred for 15 min. The organic layer was separated and aqueous layer was extracted with ethyl acetate (25 ml). The combined organic layer was washed with water (25 ml) and dried over sodium sulfate. The solvent was distilled out at 35-40° C. under reduced pressure to obtain the title compound.

Yield: 2 g $^1$H NMR: 1.27 (d, 6H), 1.47 (s, 9H), 1.50-1.58 (m, 1H), 2.38 (d, 2H), 3.37 (septet, 1H), 3.51 (s, 3H), 3.57 (s, 3H), 3.63 (bs, 1H), 3.80 (bs, 1H), 4.15-4.18 (m, 1H), 4.44-4.48 (m, 1H), 5.46 (dd, 1H), 6.64 (d, 1H), 7.09 (t, 2H), 7.65 (dd, 2H).

EXAMPLE 8

Preparation of N,N'-Dibenzylethylenediamine Rosuvastatin

Rosuvastatin t-butyl ester (1 g) was dissolved in ethanol (15 ml). The resulting solution was treated with 1 N aqueous sodium hydroxide (1.96 ml) at 25-30° C. The mixture was stirred for 1 h at 25-30° C. for completion of hydrolysis. Ethanol was rotoevaporated and the residue is diluted with DM water (25 ml) and extracted with a mixture of ethyl acetate-toluene (4:6, 2×20 ml).

To the above aqueous layer, a solution of N,N'-dibenzylethylenediamine diacetate (0.34 g dissolved in 2 ml of water) was added and stirred for 2 h. The precipitated product was filtered, washed with water and dried under vacuum at 40-45° C.

Dry Wt. 0.75 g

EXAMPLE 9

Purification of N,N'-Dibenzylethylenediamine Rosuvastatin

N,N'-dibenzylethylenediamine rosuvastatin (0.5 g) was dissolved in methanol (1 ml) and treated with ethyl acetate (5 ml) at 25-30° C. The resulting mixture was cooled to 0-5° C. and stirred for 1 h. The precipitated product was filtered and dried under vacuum.

Dry. Wt. 0.2 g, Chromatographic purity: 99.91%, Anti isomer: 0.19%.

Input Chromatographic purity: 99.33, Anti isomer: 0.66%.

PXRD (°2θ) 5.6, 10.1, 11.3, 13.0, 14.7, 15.1, 16.0, 16.3, 17.0, 17.3, 17.8, 18.6, 19.0, 21.3, 21.9, 22.5, 23.5, 25.4, 30.9, 32.7±0.2

EXAMPLE 10

Preparation of Rosuvastatin Calcium

N,N'-dibenzylethylenediamine rosuvastatin salt (2 g) was dissolved in a mixture of ethyl acetate (30 ml) and DM water (30 ml) and cooled to 0-5° C. The above cold mixture was treated with aqueous hydrochloric acid (3 ml) at 0-5° C. The resulting clear solution was stirred for 10 min. The organic layer was separated, washed with water and cooled to 0-5° C. Aqueous sodium hydroxide (1 N, 30 ml) was added to the above organic layer and stirred at room temperature for 30 min for conversion of rosuvasatin acid to it sodium salt. Toluene (70 ml) was added to the above mixture and stirred for 10 min. The aqueous layer was separated and traces of solvent were removed at 40-45° C. under vacuum. The resulting clear aqueous layer was treated with an aqueous solution of calcium chloride (1N, 3 ml) and resulting rosuvastatin calcium was filtered and dried.

Dry Wt. 0.6 g; Chromatographic purity: 99.3%.

EXAMPLE 11

Preparation of Rosuvastatin Calcium

N,N'-dibenzylethylenediamine rosuvastatin salt (1 g) was suspended in DM water(20 ml) and treated with aqueous sodium hydroxide solution (0.1N, 16.63 ml) at 25-30° C. The resulting suspension was stirred for 30 min and the undissolved matter was filtered off. The clear aqueous layer was washed twice with 30%v/v ethyl acetate/toluene (5 ml). Traces of organic solvent from aqueous layer was removed under vacuum at 40-45° C. The clear aqueous layer containing Rosuvastatin sodium was treated with aqueous solution of calcium chloride (1 N, 1.66 ml), precipitated rosuvastatin calcium was filtered, washed with water and dried.

Dry Wt. 0.35; Chromatographic purity: 99.24%; Anti isomer: 0.71%

EXAMPLE 12

Preparation of (4E)-5-{4-(4-Fluorophenyl)-6-Isopropyl-2-(N-Methyl-N-Methylsulfonylamino)Pyrimidin-5-yl}-(3S)-3-Hydroxy-4-Pentenoic Acid, (α)-Methylbenzylamine Salt (4E)-5-{4-(4-Fluorophenyl)-6-isopropyl-2-(N-methyl-N-methylsulfonylamino)-pyrimidin-5-yl}-3-hydroxy-4-pentenoic acid (100 gm, 0.228 ml) which contains predominantly S-isomer was dissolved in acetonitrile (1 litre) and R-(+)-α-methylbenzylamine (27.7 gm, 0.228 ml) was added to it dropwise over a period of 30 min during which salt precipitated out. The above suspension was heated to 70-75° C. and water (75 ml) was added to it to get a clear solution, which was subsequently cooled to 25° C. to reprecipitate the product. It was further cooled to 5-10° C., filtered and washed with chilled acetonitrile (150 ml, 5-10° C.). The product obtained was dried at 40-45° C. under vacuum to constant weight.

Yield: 95 gm, (74%)

Purity: >99.5%

Chiral Purity: >99.5% ee

SOR: $[\alpha]_{}^{20}$ +5.24 (c=1% in methanol)

$^1$HNMR (CDCl$_3$, 300 MHz): 1.20 (d, J=7 Hz, 6H, (CH$_3$)$_2$), 1.36 (d, J=7 Hz, 3H, CH$_3$), 2.0-2.12 (m, 2H, CH$_2$), 3.38-3.42 (m, 1H, —CH), 3.45 (s, 3H, CH$_3$), 3.55 (s, 3H, CH$_3$), 4.1-4.2 (m, 1H, CH), 4.29-4.45 (m, 1H, CH), 5.52 (dd, J=16; 6 Hz, 1H, CH), 6.54 (d, J=16 Hz, 1H, CH), 7.25-7.69 (m, 7H, ArH), 7.71-7.74 (m, 1H, ArH).

EXAMPLE 13

Preparation of (4E)-5-{4-(4-Fluorophenyl)-6-Isopropyl-2-(N-Methyl-N-Methylsulfonylamino]Pyrimidin-5-yl}-(3S)-3-Hydroxy-4-Pentenoic Acid (4E)-5-{4-(4-Fluorophenyl)-6-isopropyl-2-[methyl(methylsulfonyl)amino]pyrimidin-5-yl}-(3S)-3-hydroxy-4-pentenoic acid, α-methylbenzylamine salt (75 gm, 0.134 mol) was suspended in a mixture of methylene chloride (125 ml) and water (125 ml) at 25° C. The above suspension was cooled to 2-5° C. and pH was adjusted to 3-3.5 by slow addition of IN aqueous Hydrochloric acid. Thereafter the organic layer was separated, washed with water (125 ml) and evaporated to dryness to get the pure product.

Yield: 57 gm (97%).

We claim:

1. A process to prepare (3S)-5-[4-(4-fluorophenyl)-6-isopropyl-2-(N-methyl-N-methylsulfonylamino)pyrimidin-5-yl]-3-hydroxy-(4E)-pentenoic acid of Formula V,

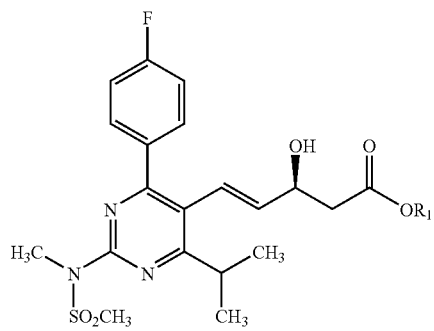

Formula V wherein R$_1$ represents C$_{1-5}$ alkyl, which comprises:

a) reacting (2E)-3-[4-(4-fluorophenyl)-6-isopropyl-2-(N-methyl-N-methanesulfonylamino)pyrimidine]-propenal of Formula II, Formula II

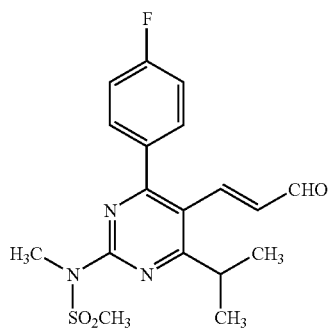

with a compound of Formula III a or III b

Formula III a

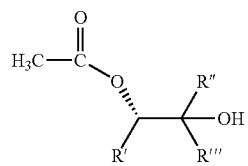

Formula III b

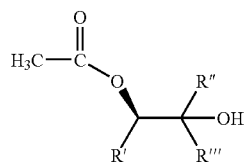

wherein R', R" and R'" represent alkyl, aralkyl, cycloalkyl, substituted cycloalkyl, phenyl, substituted phenyl, naphthyl, substituted naphthyl or heterocyclic residue, in the presence of a base selected from the group consisting of n-butyllithium, lithium hexamethyldisilazane, sodium hexamethyldisilazane and lithium diisopropylamine and an organic solvent, in the absence of $MgBr_2$, to produce a diastereomeric mixture of compounds of Formula IV a or IV b at a temperature in the range of −78° C. to +20° C.;

Formula IV a

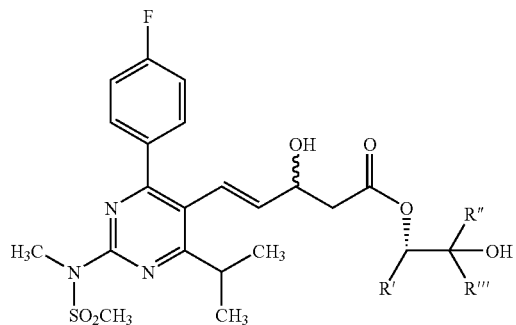

Formula IV b

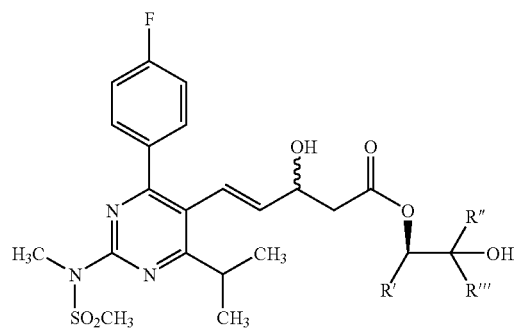

wherein R', R" and R'" are defined as above, b) hydrolyzing the mixture of compounds of Formula IVa or IVb to its corresponding acid obtaining a mixture of compounds of Formula X isomers

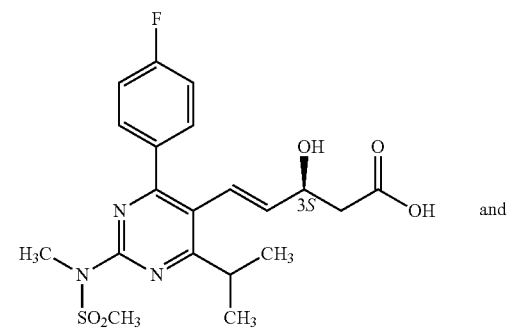

and

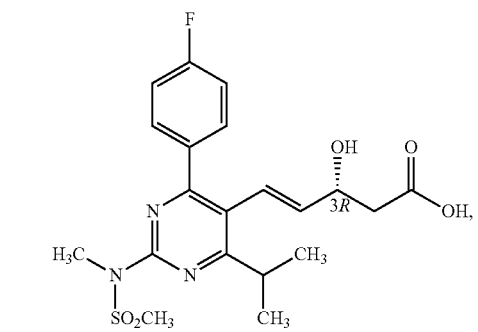

c) purifying compounds of Formula X by using optically pure precipitating agents in a mixture of organic solvent and water to get enantiomerically pure compound of Formula XI; and

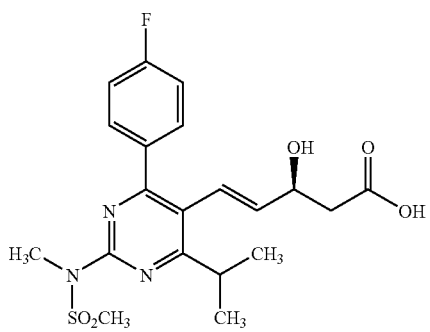

Formula XI d) esterifying the compound of Formula XI to get enantiomerically pure compound of Formula V.

2. The process according to claim 1, wherein the organic solvent in step (a) is selected from the group consisting of ether, tetrahydrofuran, heptane, hexane and mixture thereof.

3. The process according to claim 1, wherein enantiomerically pure compound of Formula V is prepared by
   a) purifying by crystallizing the diastereomeric mixture of compounds of Formula IVa or Formula IVb obtained in step (a) to give diastereomerically pure compound of formula IVc or IVd; and

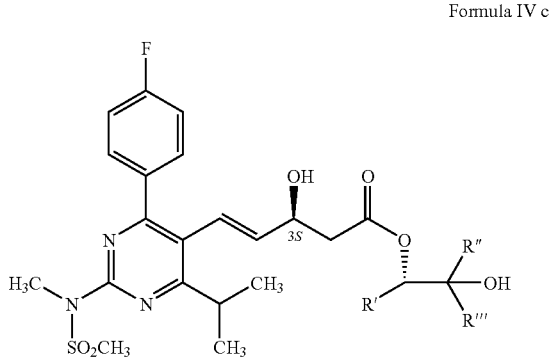

Formula IV c

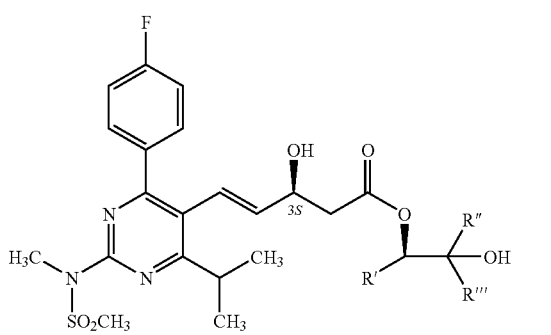

Formula IV d b) treating the compound of Formula IV c or Formula IV d with a lower alcohol in the presence of a base.

4. The process according to claim 3, wherein the purification is carried out in a solvent selected from the group consisting of hexane, ethyl acetate, toluene, MTBE, acetone, acetonitrile, butylacetate, isopropylether and mixtures thereof.

5. The process according to claim 3, wherein the lower alcohol is selected from the group consisting of methanol and ethanol.

6. The process according to claim 3, wherein the base is selected from the group consisting of potassium carbonate and sodium carbonate.

7. The process according to claim 1, optically pure precipitating agent is selected from the group consisting of (+)/(−) phenylalkylamine, substituted phenylalkylamine, (+)/(−) Ephedrine, (+)/(−)1-amino-1-butanol, (+)/(−)Quinine, (+)Cinchodine, (−)Brucine and (+)Dehydroabietylamine.

8. The process according to claim 1, wherein the organic solvent in step (a) is selected from the group consisting of acetonitrile, tetrahydrofuran, ethylacetate, methanol, ethanol, and isopropyl alcohol.

9. The process according to claim 1, wherein (3S)-5-[4-(4-fluorophenyl)-6-isopropyl-2-(N-methyl-N-methylsulfonylamino)pyrimidin-5-yl]-3-hydroxy-(4E)-pentenoic acid of Formula XI, is further converted to Rosuvastatin calcium of Formula I,

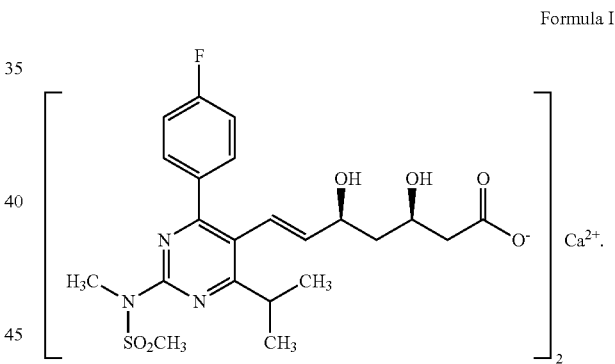

Formula I

10. The process according to claim 1, wherein the base used in step (a) is lithium hexamethyldisilazine.

11. The process according to claim 1, optically pure precipitating agent is (R)-1-phenylethylamine.

* * * * *